United States Patent
Andrew et al.

(10) Patent No.: US 8,366,700 B2
(45) Date of Patent: Feb. 5, 2013

(54) LIPOSUCTION OF VISCERAL FAT USING TISSUE LIQUEFACTION

(75) Inventors: Mark S. Andrew, Haddonfield, NJ (US); Luis A. Davila, Alpharetta, GA (US)

(73) Assignee: Andrew Technologies, LLC, New York, NY (US)

( * ) Notice: Subject to any disclaimer, the term of this patent is extended or adjusted under 35 U.S.C. 154(b) by 671 days.

(21) Appl. No.: 12/366,983

(22) Filed: Feb. 6, 2009

(65) Prior Publication Data

US 2009/0192498 A1  Jul. 30, 2009

Related U.S. Application Data

(63) Continuation-in-part of application No. 12/112,233, filed on Apr. 30, 2008.

(60) Provisional application No. 61/065,187, filed on Feb. 7, 2008, provisional application No. 60/915,027, filed on Apr. 30, 2007.

(51) Int. Cl.
*A61M 1/00* (2006.01)
(52) U.S. Cl. .............. 604/542; 604/22; 604/23; 604/24; 604/25; 604/26; 604/27; 604/28; 604/29; 604/30; 604/31; 604/32; 604/33; 604/34; 604/35; 604/39; 604/42; 604/43; 604/264; 604/523; 606/127; 606/128; 606/159; 606/167; 606/190
(58) Field of Classification Search .................. 604/523, 604/542
See application file for complete search history.

(56) References Cited

U.S. PATENT DOCUMENTS

| | | | |
|---|---|---|---|
| 5,616,120 | A | 4/1997 | Andrew et al. |
| 6,074,358 | A | 6/2000 | Andrew et al. |
| 6,319,222 | B1 | 11/2001 | Andrew et al. |
| 6,544,211 | B1 | 4/2003 | Andrew et al. |
| 6,676,629 | B2 | 1/2004 | Andrew et al. |
| 7,011,644 | B1 | 3/2006 | Andrew et al. |
| 2002/0188280 | A1 | 12/2002 | Nguyen |
| 2006/0100606 | A1 | 5/2006 | Dobak |

FOREIGN PATENT DOCUMENTS

| | | | |
|---|---|---|---|
| WO | 9005493 | | 5/1990 |
| WO | WO 01/76518 | * | 4/2000 |
| WO | 0176518 | | 10/2001 |
| WO | 2007087404 | | 8/2007 |
| WO | 2008134713 | | 11/2008 |

OTHER PUBLICATIONS

Jong-Ha Chung, Design of the Dexterous Manipulator for Minimally Invasive Surgery, Department of Mechanical Engineering, Korea Advanced Institute of Science and Technology, (undated).

(Continued)

*Primary Examiner* — Tatyana Zalukaeva
*Assistant Examiner* — Ilya Treyger
(74) *Attorney, Agent, or Firm* — Proskauer

(57) ABSTRACT

Visceral fat may be removed from a subject using a cannula that has an interior cavity and an orifice configured to permit material to enter the cavity. This is accomplished by generating a negative pressure in the cavity so that a portion of the tissue is drawn into the orifice. Fluid is then delivered in pulses, via a conduit, so that the fluid exits the conduit within the cavity and impinges against the portion of the tissue that was drawn into the orifice. The fluid is delivered at a pressure and temperature that causes the visceral fat to soften, liquefy, or gellify, without damaging the subject's internal organs that are in the vicinity of the visceral fat. The visceral fat that has been softened, liquefied, or gellified is then suctioned away.

7 Claims, 11 Drawing Sheets

OTHER PUBLICATIONS

Nakamura, R, Multi-DOF Forceps Manipulator Systems for Laparoscopic Surgery-Mechanism miniaturized & Evaluation of New Interface, Proc of Fourth International Conference on Medical Image Computing and Computer assisted Interventions (MICCA12001), Utecht, the Netherlands, Oct. 14-17, 2001: pp. 606-613.

Search Report and Written Opinion from corresponding application PCT/US2009/033372.

* cited by examiner

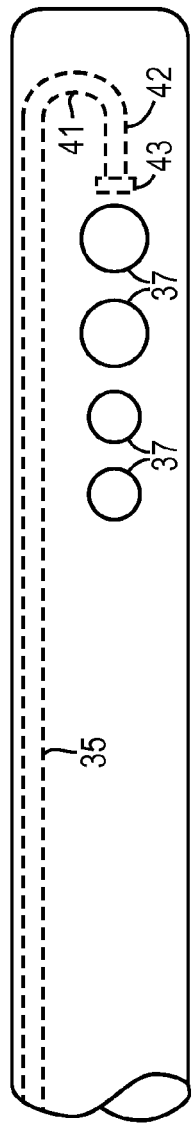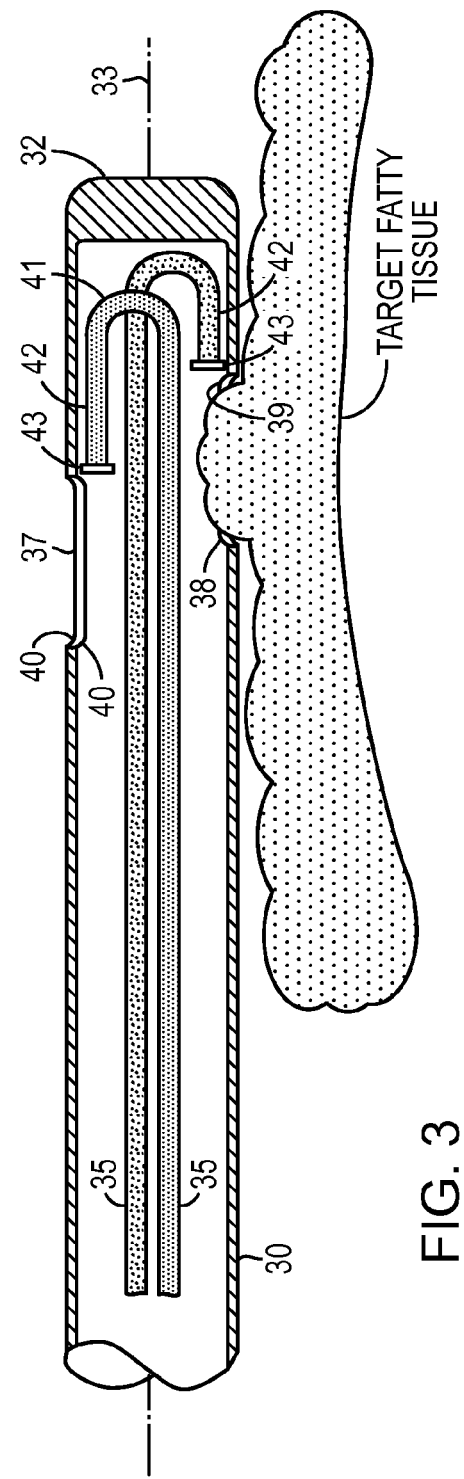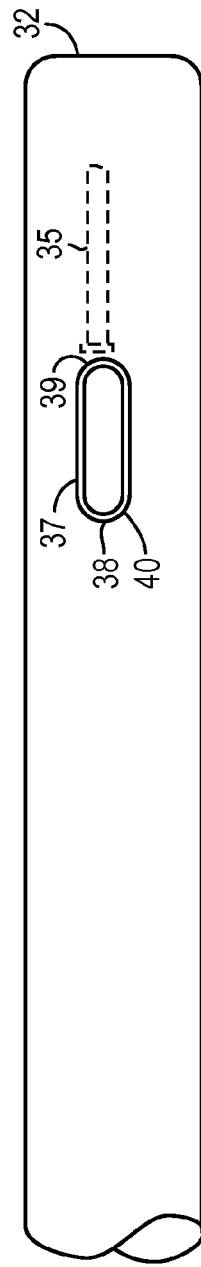

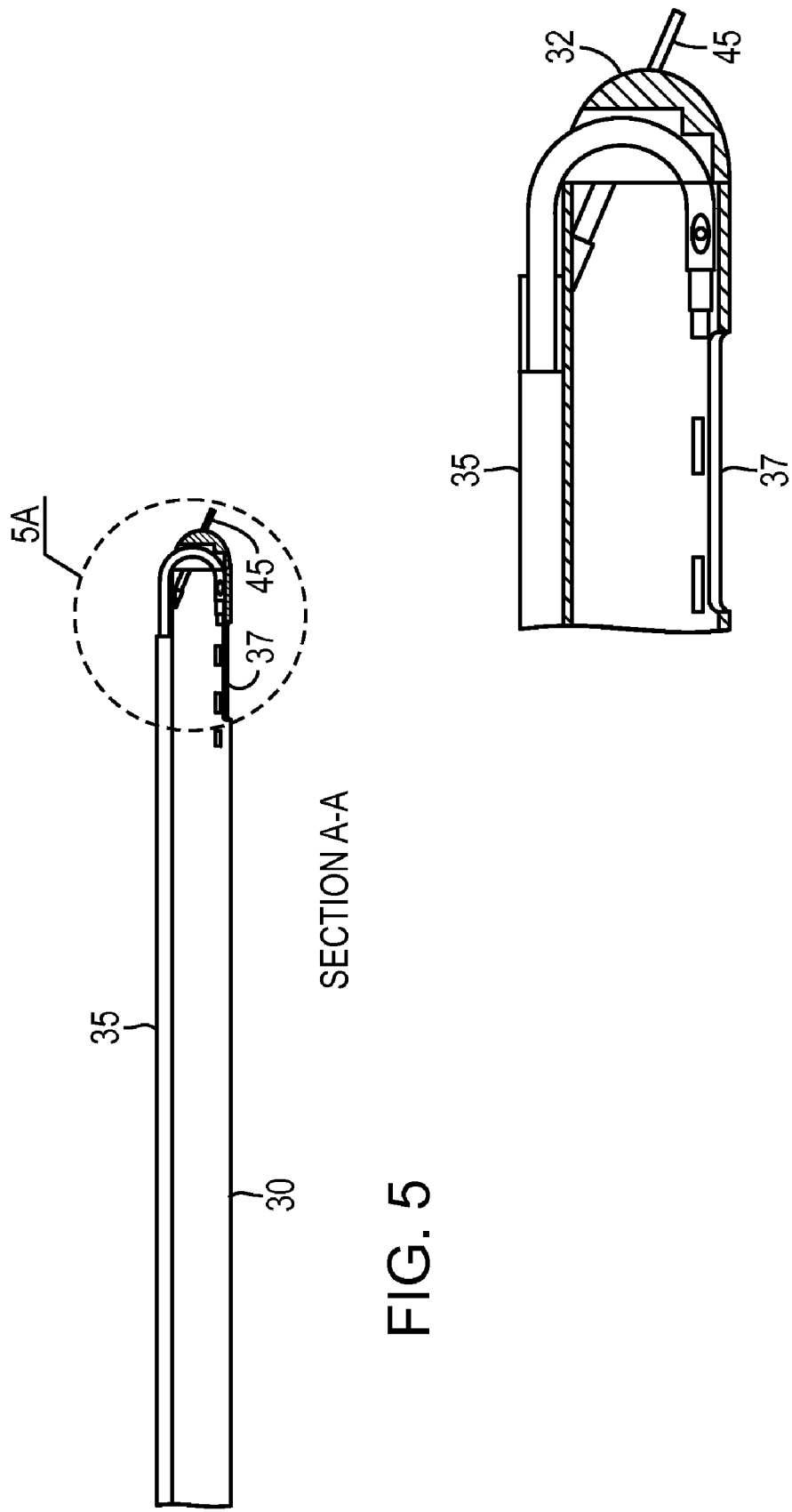

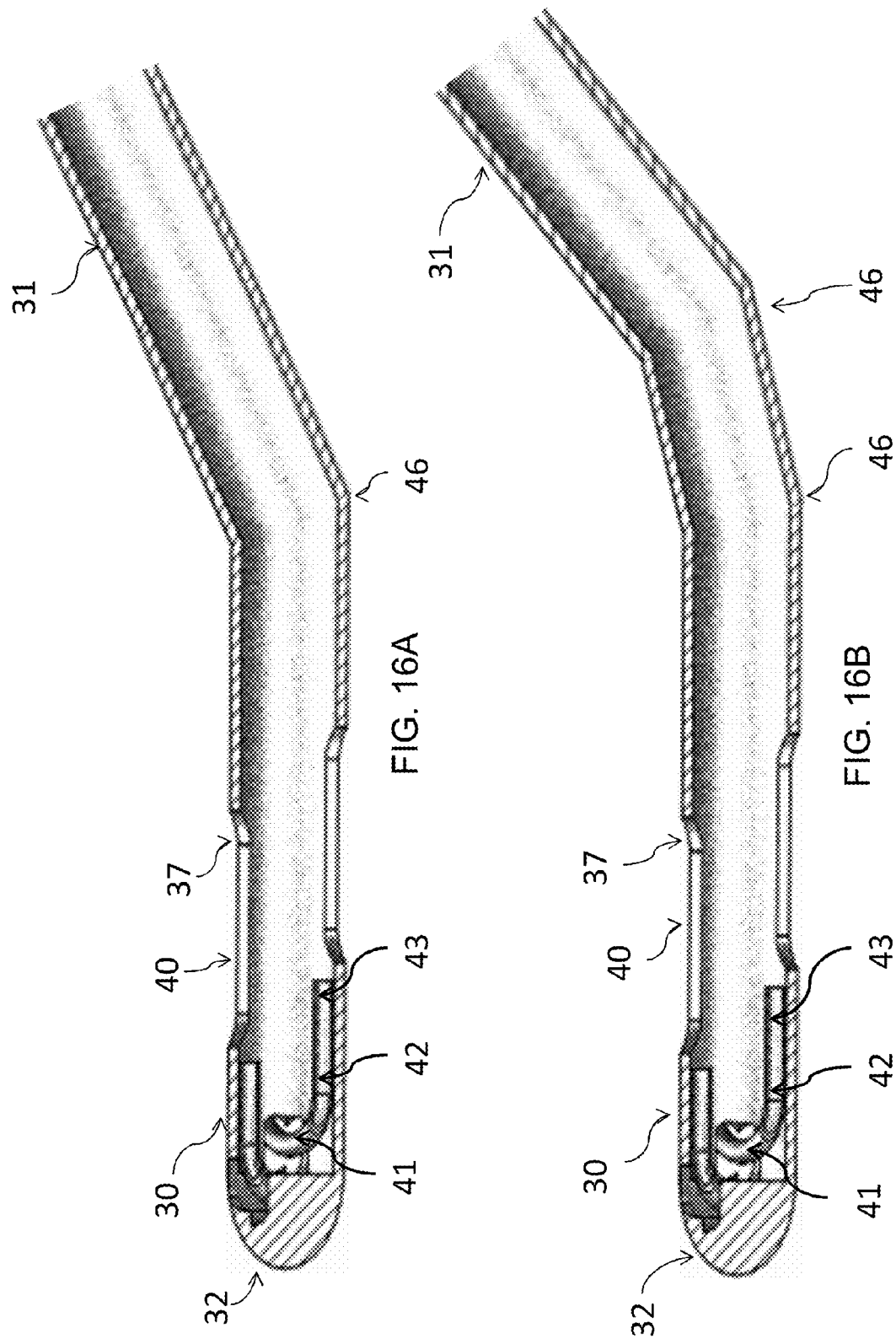

LIPOSUCTION OF VISCERAL FAT USING TISSUE LIQUEFACTION

CROSS REFERENCE TO RELATED APPLICATIONS

This application claims the benefit of U.S. provisional application 61/065,187, filed Feb. 7, 2008; and this application is also a continuation-in-part of U.S. application Ser. No. 12/112,233, filed Apr. 30, 2008, which claims the benefit of U.S. provisional application 60/915,027, filed Apr. 30, 2007.

BACKGROUND

It has come to light in the past 5 years that visceral fat is harmful to general health, whereas subcutaneous fat is not. Visceral fat is now viewed as not just an inert blob of fat, but as another endocrine organ, a "bad" endocrine organ. The visceral fat secretes chemical mediators which are believed to cause insulin resistance. Therefore visceral fat is now viewed as a culprit in the pathogenesis of diabetes mellitus type II. Also, visceral fat is suspected to be a possible contributor to cardiovascular disease, cancer, and even aging itself.

Liposuction, also known as lipoplasty (fat modeling), liposculpture, or suction lipectomy (suction-assisted fat removal) is a cosmetic surgery operation that removes subcutaneous fat from many different sites on the human body (e.g., the chest, buttocks, hips, thighs, or arms). The typical liposuction procedure relies on the shearing action of a sharp-edged instrument to shear away the fatty deposits. The sheared fatty deposits are then suctioned away into orifices on the cannula. This process is labor intensive for the surgeon, traumatic to the patient, and very time consuming.

Typical liposuction tools and methods cannot be used for visceral fat lipectomy in the same manner as they are used to remove subcutaneous fat, since visceral fat is attached to sensitive internal organs that will not tolerate the repeated thrusting and shearing required with traditional lipectomy.

SUMMARY

With the methods and apparatuses described herein, visceral fat is drawn into orifices in a cannula, and a heated solution is impinged against those portions of visceral fat. The heated solution liquefies or gellifies parts of the visceral fat, so they can be removed from the patient's body more easily.

BRIEF DESCRIPTION OF THE DRAWINGS

FIG. 2 is a detail of the distal end of the FIG. 1 embodiment.

FIG. 3 is a section view of alternative configuration for the distal end of the FIG. 1 embodiment.

FIG. 4 is a detail of another alternative configuration for the distal end of the FIG. 1 embodiment.

FIGS. 5 and 5A show another embodiment of a tissue liquefaction system, which includes a forward-facing external tumescent spray applicator.

FIG. 16A shows an alternative cannula configuration with a single bend.

FIG. 16B shows an alternative cannula configuration with two bends.

DETAILED DESCRIPTION OF THE PREFERRED EMBODIMENTS

The embodiments described below generally involve the delivery of pressurized heated biocompatible fluid to heat targeted tissue and soften, gellify, or liquefy the target tissue for removal from a living body. The heated biocompatible fluid is preferably delivered as a series of pulses, but in alternative embodiments may be delivered as a continuous stream. After the tissue has been softened, gellified, or liquefied, it is sucked away out of the subject's body.

The interaction with the subject takes place at a cannula 30, examples of which are depicted in FIGS. 1-4. The distal end of cannula is preferably smooth and rounded for introduction into the subject's body, and the proximal end of the cannula is configured to mate with a handpiece 20. The cannula 30 has an interior cavity with one or more orifice ports 37 that open into the cavity. These orifices 37 are preferably located near the distal portion of the cannula 30. When a low pressure source is connected up to the cavity via a suitable fitting, suction is generated which draws target tissue into the orifice ports 37.

Figure 7:
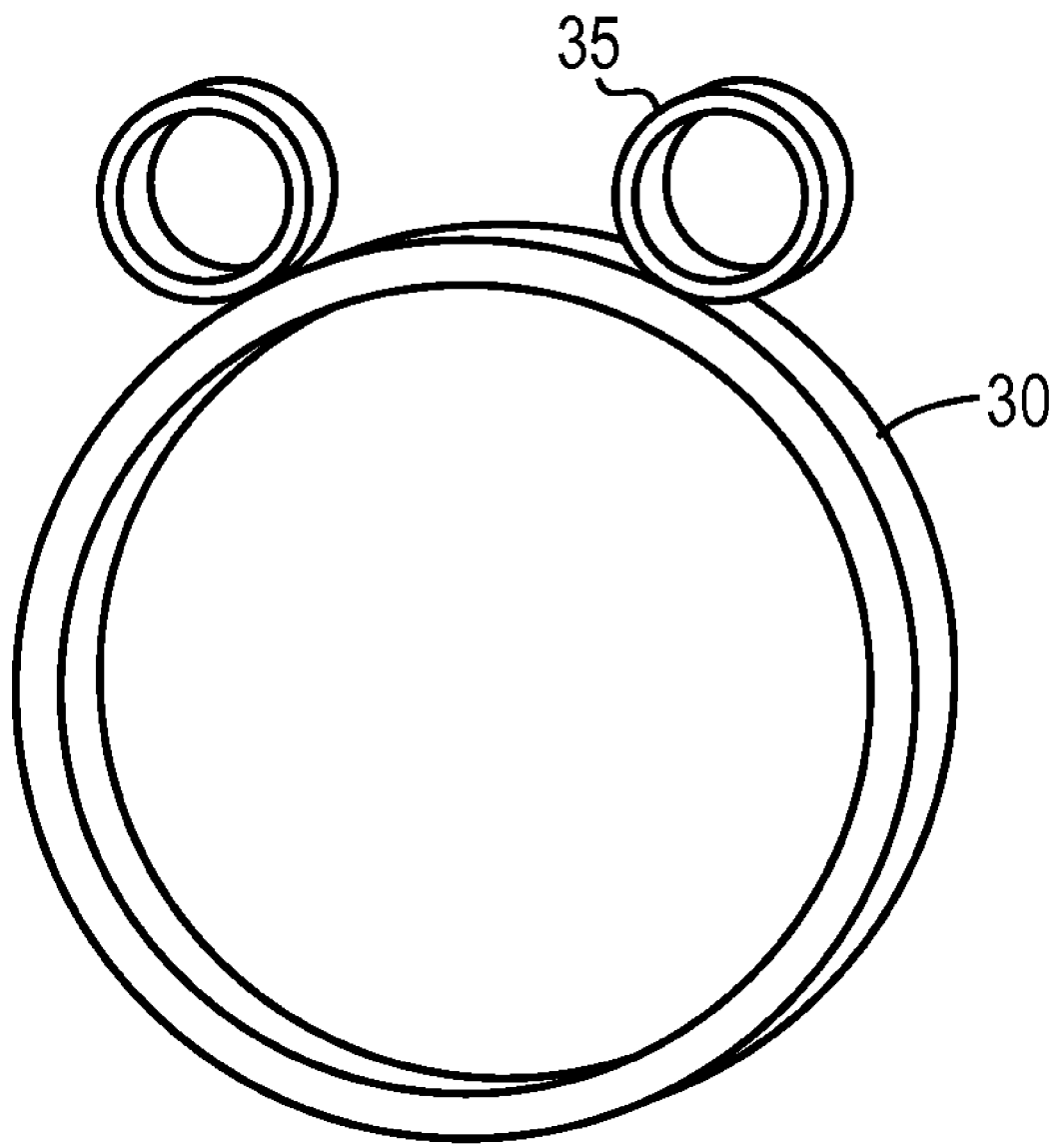
FIG. 7 shows how the cannula can be configured with external fluid-supply paths, in less preferred embodiments.
Figure 8:
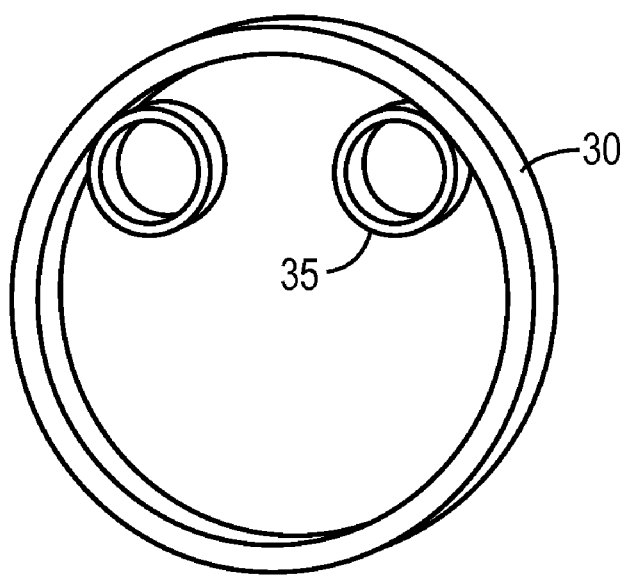
FIG. 8 shows how the cannula can be configured with the fluid supply paths internal to the suction path.
Figure 9:
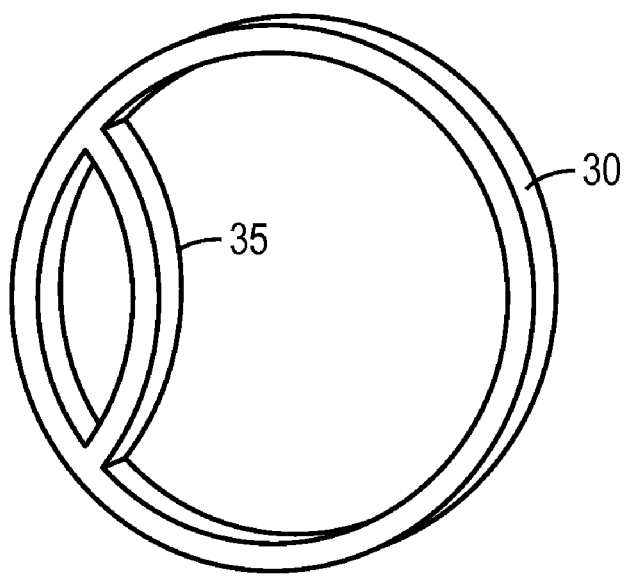
FIG. 9 shows a cannula with a single fluid supply tube internal to the suction path

The cannula also includes one or more fluid supply tubes 35 that direct the heated fluid onto the target tissue that has been drawn into the cavity. These fluid supply tubes are preferably arranged internally to the outside wall of the cannula (as shown in FIG. 8), but in alternative embodiments may be external to the cannula for a portion of the length of the supply tube (as shown in FIG. 7). The heated fluid supply tubes 35 preferably terminate within the outside wall of the cannula, in the vicinity of the suction orifice ports 37. The fluid supply tubes 35 are arranged to spray the fluid across the orifice ports 37 so that the fluid strikes the target tissue that has been drawn into the cavity. Delivery of the tissue fluid stream is preferably contained within the outer wall of the cannula.

The fluid delivery portion may be implemented using a fluid supply reservoir 4, a heat source 8 that heats the fluid in the reservoir 4, and a temperature regulator 9 that controls the heat source 8 as required to maintain the desired temperature. The heated fluid from the fluid supply 4 is delivered under pressure by a suitable arrangement such as a pump system 19 with a pressure regulator 11. Optionally, a heated fluid metering device 12 may also be provided to measure the fluid that has been delivered.

Pump 19 pumps the heated fluid from the reservoir or fluid supply source 4 down the fluid supply tubes 35 that run from the proximal end of the cannula 30 down to the distal end of the cannula. Near the distal tip of the cannula, these fluid supply tubes preferably make a U-turn so as to face back towards the proximal end of the cannula 30. As a result, when the heated fluid exits the supply tube 35 at the supply tube's delivery orifice 43, the fluid is traveling in a substantially distal-to-proximal direction. Preferably, the pump delivers a pressurized, pulsating output of heated fluid down the supply tube 35 so that a series of boluses of fluid are ejected from the delivery orifice 43, as described in greater detail below.

The vacuum source and the fluid source interface with the cannula 30 via a handpiece 20. The heated solution supply is connected on the proximal side of hand piece 20 with a suitable fitting, and a vacuum supply is also connected to the proximal side of handpiece 20 with a suitable fitting. Cannula 30 is connected to the distal side of hand piece 20 with suitable fittings so that (a) the heated fluid from the fluid supply is routed to the supply tubes 35 in the cannula and (b) the vacuum is routed from the vacuum source 14 to the cavity in the cannula, to evacuate material from the cavity.

More specifically, the pressurized heated solution that is discharged from pump 19 is connected to the proximal end of the handle 20 via high pressure flexible tubing, and routed through the handpiece 20 to the cannula 30 with an interface made using an appropriate fitting. The vacuum source 14 is connected to an aspiration collection canister 15, which in turn is connected to the proximal end of the handle via flexible tubing 16, and then routed through the handpiece 20 to the cannula 30 with an interface made using an appropriate fitting. The pressurized fluid supply line connection between the handle and the cannula 30 may be implemented using a high pressure quick disconnect fitting located at the distal end of the handle, and configured so that once the cannula is inserted into the distal end of the handle it aligns and connects with both the fluid supply and the vacuum supply. The cannula 30 may be held in place on the handle 20 by an attachment cap.

As best seen in FIG. 3, after the cannula 30 is inserted into the body; vacuum source 14 creates a low pressure region within cannula 30 such that the target fatty tissue is drawn into the cannula 30 through suction orifice 37. The geometry of the end of the supply tube 35 is configured so the trajectory of the boluses leaving the delivery orifice will strike the fatty tissue that has been drawn into the cannula 30 through suction orifice 37. For that purpose, the end of the supply tube preferably points in direction that is substantially parallel to that of the inside wall of the cannula 30 where it is affixed. Preferably, it is oriented that the stream flows across the orifice in a distal to proximal direction. This placement of the tip 43 of the supply tube 35 advantageously maximizes the energy transfer (kinetic and thermal) to the fatty tissues, minimizes fluid loss, and helps prevent clogs by pushing the heated fluid and the liquefied/gellified/softened material in the same direction that it is being pulled by the vacuum source.

Once the targeted fatty tissue enters the suction orifice 37, it is repeatedly struck by the boluses of heated fluid that are exiting the supply tubes 35 via the delivery orifice 43. The target fatty tissue is heated by the impinging boluses of fluid and is softened, gellified, or liquefied. After that occurs, the loose material in the cavity (i.e., the heated fluid and the portions of tissue that were dislodged by the fluid) is drawn away from the surrounding tissue by the vacuum source 14, and deposited into the canister 15 (shown in FIG. 1).

Advantageously, fat is more readily softened, gellified, or liquefied (as compared to other types of tissue), so the process targets fat more than other types of tissue. Note that the distal-to-proximal direction of the boluses is the same as the direction that the liquefied/gellified tissue travels when it is being suctioned out of the patient via the cannula 30. By having the fluid stream flow in the distal to proximal direction, additional energy (vacuum, fluid thermal and kinetic) is transferred in the same direction, which aids in moving the aspirated tissues through the cannula. This further contributes to reducing clogs, which can reduce the time it takes to perform a procedure.

Notably, in the embodiments described herein, the majority of the fluid stays within the interior of the cannula during operation (although a small amount of fluid may escape into the subject's body through the suction orifices 37). This is advantageous because minimizing fluid leakage from the cannula into the tissue maximizes the energy transfer (thermal and kinetic) from the fluid stream to the tissue drawn into the cannula for liquefaction.

The fluid supply portion of the system will now be described with additional detail. FIG. 3 depicts a cut-away view of an embodiment of the cannula 30 that has two supply tubes 35. Each of the supply tubes 35 is provided for delivering the heated fluid. Supply tube 35 extends from the proximal portion of cannula 30 to the distal tip 32 of cannula 30. Supply tube 35 extends along the interior of cannula 35 and may be a separate structure secured to the interior of cannula 35 or lumen integrated into the wall of cannula 30. Supply tube 35 is configured to deliver heated biocompatible solution for liquefying tissue. The heated solution is delivered through hand piece 20 and into supply tube 35.

The supply tube 35 extends longitudinally along axis 33 from the proximal end 31 to the distal tip 32. Supply tube 35 includes U-bend 41, effectively turning the run of the supply tube 35 along the inner wall of the distal tip 32. Adjacent the terminal end of u-bend 41 is supply tube terminal portion 42, which includes delivery orifice 43. Delivery orifice 43 is configured to direct heated solution exiting supply tube 35 across suction orifice port 37. In this manner, supply tube 35 is configured to direct the fluid onto a target tissue that has entered the cannula 30 through the suction orifice port 37.

Heated solution supply tube 35 may be constructed of surgical grade tubing. Alternatively, in embodiments wherein the heated solution supply tube is integral to the construction of cannula 30, the supply tube 35 may be made of the same material as cannula 30. The diameter of supply tube 35 may be dependent on the target tissue volume requirements for the heated solution and on the number of supply tubes required to deliver the heated solution across the one or more suction orifice ports 37. The cannula 30 tube diameters vary with the cannula outside diameters and those can range from 2-6 mm. The fluid supply tube 35 diameters are dependent on the inside diameters of the tubes. A preferred range of supply tube 35 diameters is from about 0.008" to 0.032". In one preferred embodiment, the supply tube 35 is a 0.02" diameter for the length of the cannula 30, with an exit nozzle formed by reducing the diameter to 0.008" over the last 0.1". The shape and size of delivery orifice 43 may vary, including reduced diameter and flattened configurations, with the reduced diameter being preferred.

In alternative embodiments, the cannula 30 may have a different number of heated solution supply tubes 35, each corresponding to a respective suction orifice port. For example, a cannula 30 with three suction orifice ports 37 would preferably include three heated solution supply tubes 35. Additionally, heated solution supply tubes may be added to accommodate one or more suction orifice ports, e.g., when four suction orifice ports are provided, four heated solution supply tubes may be provided. In another embodiment, a supply tube 35 may branch into multiple tubes, each branch servicing a suction orifice port. In another embodiment, one or more supply tubes may deliver the heated fluid to a single orifice port. In yet another embodiment, supply tube 35 may be configured to receive one or more fluids in the proximal portion of cannula 30 and deliver the one or more fluids though a single delivery orifice 43. In another embodiment, the cannula may be attached to an endoscope or other imaging device. In yet another embodiment depicted in FIGS. 5 and 5A, cannula 30 may include a forward-facing external fluid delivery applicator 45 in addition to the distal-to-proximal fluid supply tube 35.

The heated fluid should be biocompatible, and may comprise a sterile physiological serum, saline solution, glucose solution, Ringer-lactate, hydroxyl-ethyl-starch, or a mixture of these solutions. The heated biocompatible solution may comprise a tumescent solution. The tumescent solution may comprise a mixture of one or more products producing different effects, such as a local anesthetic, a vasoconstrictor, and a disaggregating product. For example, the biocompatible solution may include xylocalne, marcaine, nesacaine, Novocain, diprivan, ketalar, or lidocaine as the anesthetic agent. Epinephrine, levorphonal, phenylephrine, athyl-adrianol, or ephedrine may be used as vasoconstrictors. The heated biocompatible fluid may also comprise saline or sterile water or may be comprised solely of saline or sterile water.

Figure 14:
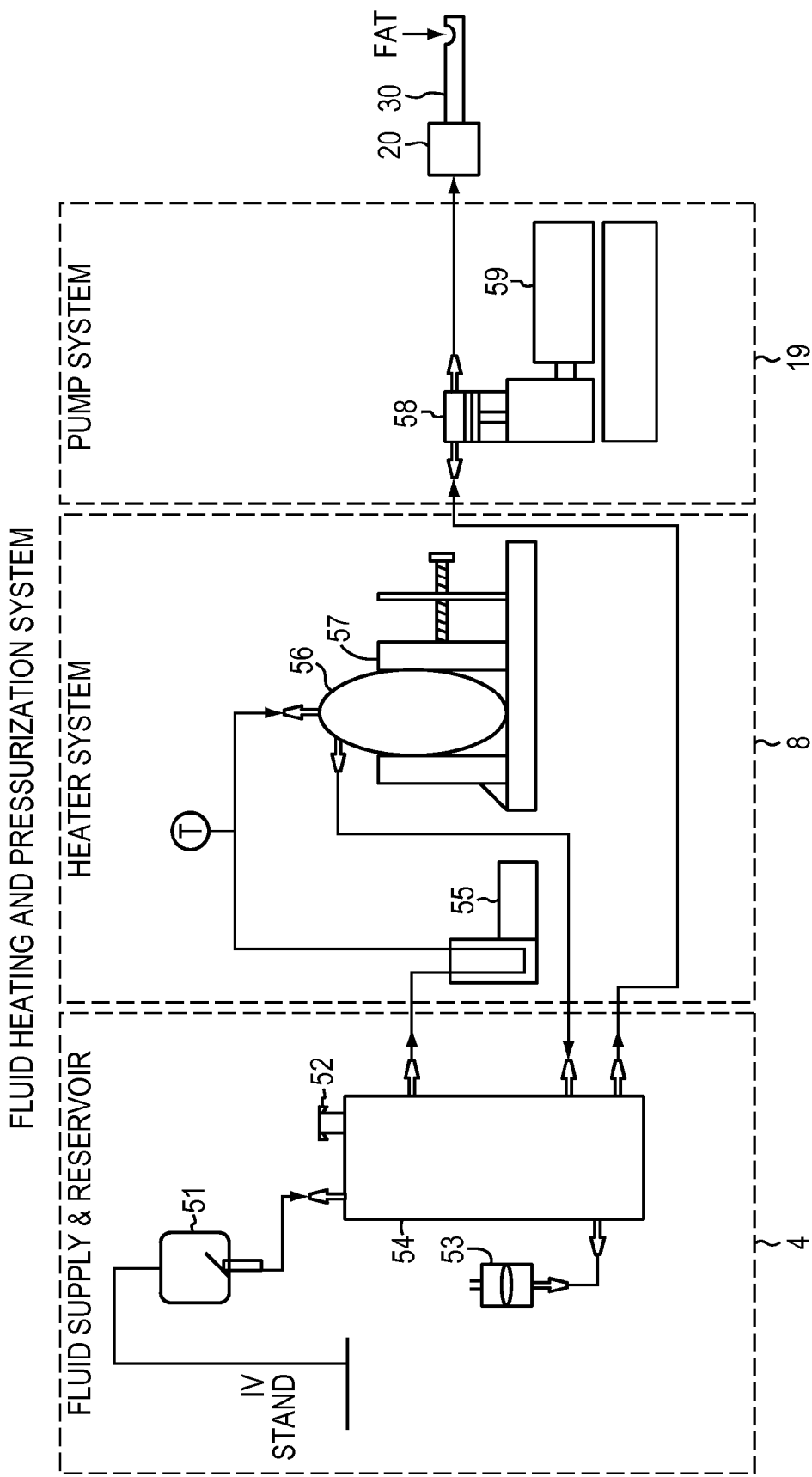
FIG. 14 is a block diagram of a suitable fluid heating and pressurization system.

FIG. 14 depicts one example of a suitable way to heat the fluid and deliver it under pressure. The components in FIG. 14 operate using the following steps: Room temperature saline drains from the IV bag 51 into mixing storage reservoir 54. Once the fluid in the reservoir 54 reaches a fixed limit, the fixed speed peristaltic pump 55 of the heater system 8 moves fluid from the reservoir 54 to the heater bladder 56. The fluid is circulated through the bladder and is heated by the electric panels 57 of the heater system 8. The heated fluid is returned back to the reservoir 54 and mixes with the other fluid in the storage container. The fixed speed peristaltic pump 55 continues to circulate fluid to the heater unit and back into the reservoir 54. The continuous circulation of fluid provides a very stable and uniform heated fluid volume supply. Temperature control may be implemented using any conventional technique, which will be readily apparent to persons skilled in the relevant arts, such as a thermostat or a temperature-sensing integrated circuit. The temperature may be set to a desired level by any suitable user interface, such as a dial or a digital control, the design of which will also be apparent to persons skilled in the relevant arts.

The pump 58 may be a piston-type pump that draws heated fluid from the fluid reservoir 54 into the pump chamber when the pump plunger travels in a backstroke. The fluid inlet to the pump has an in-line one-way check valve that allows fluid to be suctioned into the pump chamber, but will not allow fluid to flow out. Once the pump plunger backstroke is completed, the forward travel of the plunger starts to pressurize the fluid in the pump chamber. The pressure increase causes the one-way check valve at the inlet of the pump 58 to shut preventing flow from going out the pump inlet. As the pump plunger continues its forward travel the fluid in the pump chamber increases in pressure. Once the pressure reaches the preset pressure on the pump discharge pressure regulator the discharge valve opens. This creates a bolus of pressurized heated fluid that travels from the pump 58 through cannula handle 20 and from there into the supply tube 35 in the cannula 30. After the pump plunger has completed its forward travel the fluid pressure decreases and the discharge valve shuts. These steps are then repeated to generate a series of boluses. Suitable repetition rates (i.e., pulse rates) are discussed below.

One example of a suitable approach for implementing the positive displacement pump is to use an off-set cam on the pump motor that causes the pump shaft to travel in a linear motion. The pump shaft is loaded with an internal spring that maintains constant tension against the off-set cam. When the pump shaft travels backwards towards the off-set cam it creates a vacuum in the pump chamber and suctions heated saline from the heated fluid reservoir. A one-way check valve is located at the inlet port to the pump chamber, which allows fluid to flow into the chamber on the backstroke and shuts once the fluid is pressurized on the forward stroke. Multiple inlet ports can allow for either heated or cooled solutions to be used. Once the heated fluid has filled the pump chamber at the end of the pump shaft backwards travel, the off-set portion of the cam will start to push the pump shaft forward. The heated fluid is pressurized to a preset pressure (e.g. 1100 psi) in the pump chamber, which causes the valve on the discharge port to open, discharging the pressurized contents of the pump chamber to fluid supply tubes 35. Once the pump plunger completes its full stroke based on the off-set of the cam, the pressure in the pump chamber decreases and the discharge valve closes. As the cam continues to turn the process is repeated. The pump shaft can be made with a cut relief, which will allow the user to vary the boluses size. The cut off on the shaft will allow for all the fluid in the pumping chamber to be ported through the discharge path to the supply tubes or a portion of the pressurized fluid to be ported back to the reservoir.

The heated biocompatible solution in a tissue liquefaction system is preferably delivered in a manner optimized for softening, gellifying, or liquefying the target tissue. Variable parameters include, without limitation, the temperature of the solution, the pressure of the solution, the pulse rate or frequency of the solution, and the duty cycle of the pulses or boluses within a stream. Additionally, the vacuum pressure applied to the cannula through vacuum source 14 may be optimized for the target tissue.

It has been found that for liposuction procedures targeting subcutaneous fatty deposits within the human body, the biocompatible heated solution should preferably be delivered to the target fatty tissue at a temperature between 75 and 250 degrees F., and more preferably between 110 and 140 degrees F. A particular preferred operating temperature for the heated solution is about 120 degrees F., since this temperature appears very effective and safe. Also, for liquefaction of fatty deposits the pressure of the heated solution is preferably between about 200 and about 2500 psi, more preferably between about 600 and about 1300 psi, and still more preferably between about 900 and about 1300 psi. A particular preferred operating pressure is about 1100 psi, which provides the desired kinetic energy while minimizing fluid flow. The pulse rate of the solution is preferably between 20 and 150 pulses per second, more preferably between 25 and 60 pulses per second. In some embodiments, a pulse rate of about 40 pulses per second was used. And the heated solution may have a duty cycle (i.e., the duration of the pulses divided by the period at which the pulses are delivered) of between 1-100%. In preferred embodiments, the duty cycle may range between 30 and 60%, and more particularly between 30 and 50%.

Figure 15:
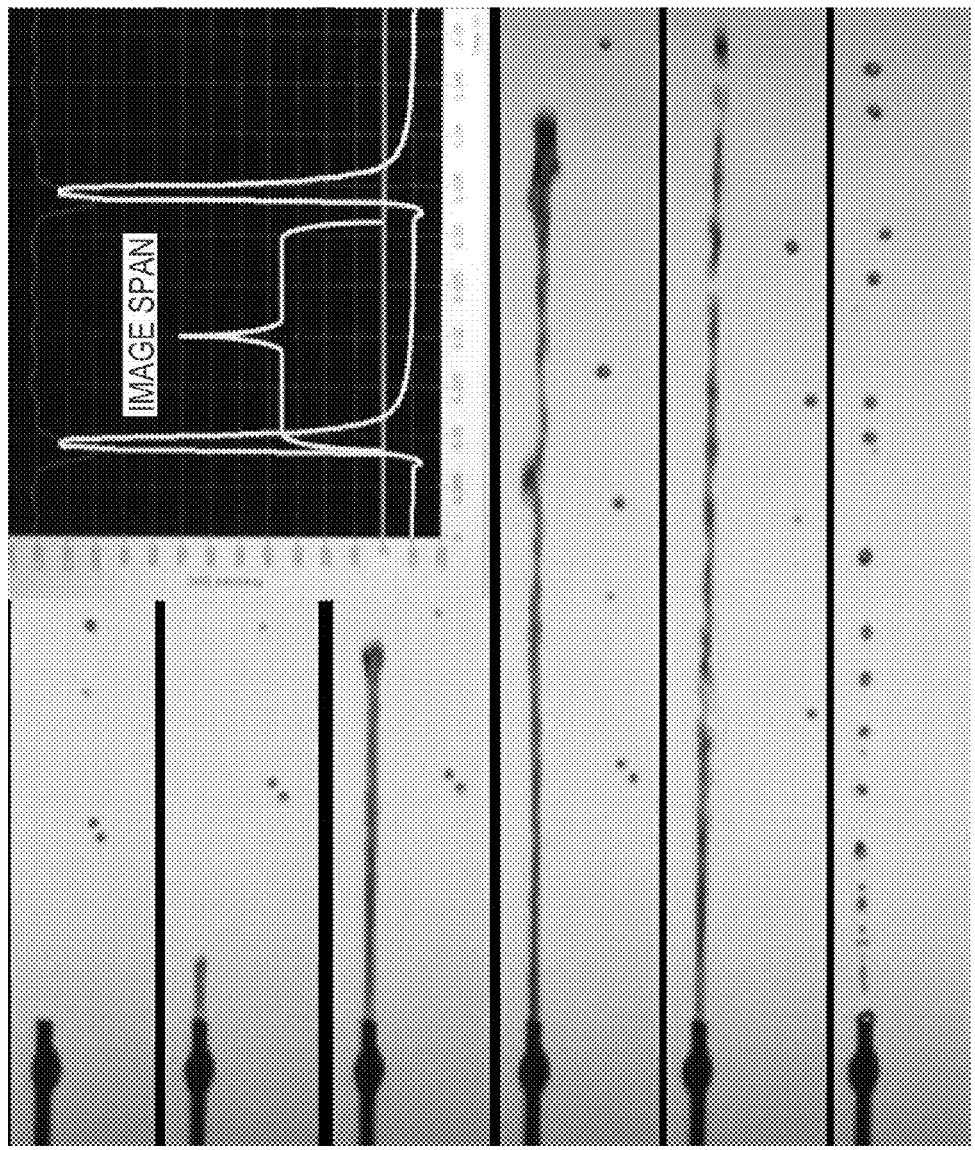
FIG. 15 shows a high speed camera fluid supply image and pressure rise graph.

In preferred embodiments, the rise rate (i.e., the speed with which the fluid is brought to the desired pressure) is about 1 millisecond or faster. This may be accomplished by having a standard relief valve that opens once the pressure in the pump chamber reaches the set point (which, for example, may be set to 1100 psi). As shown in FIG. 15, the pressure increase is almost instantaneous, as evidenced by the spike representing the rise rate in the pressure rise graph (inset). FIG. 15 further illustrates how the fluid exits the fluid supply tubes during a very short time span.

Returning now to the suction subsystem, FIG. 3 depicts an expanded cut-away view of an embodiment that includes two suction orifices. As shown, the cannula 30 has two suction orifices 37 located near the distal region of the cannula 30 and proximal to distal tip 32. Suction orifice ports 37 may be positioned in various configurations about the perimeter of the distal region of cannula 30. In the illustrated embodiment, the suction orifice ports 37 are on opposite sides of tile cannula 30, but in alternative embodiments they may be positioned differently with respect to each other. Suction orifice ports 37 are configured to allow fatty tissue to enter the orifices in response to low pressure within the cannula shaft created by vacuum supply 14. The material that is located in the cavity (i.e., tissue that has been dislodged and the heated fluid that exited the supply tube 35) is then suctioned away in a proximal direction up through the cannula 30, the handpiece 20, and into the canister 15 (all shown in FIG. 1). A conventional vacuum pump (e.g., the AP-III HK Aspiration Pump from HK surgical) may be used for the vacuum source.

In preferred embodiments, the aspiration vacuum that sucks the liquefied/gellified tissue back up through the cannula ranges from 0.33-1 atmosphere (1 atmosphere=760 mm Hg). Varying this parameter is not expected to effect any significant changes in system performance. Optionally, the vacuum level may be adjustable by the operator during the procedure. Because reduced aspiration vacuum is expected to lower blood loss, operator may prefer to work at the lower end of the vacuum range.

Returning to FIGS. 1-4, the cannula 30 and handpiece 20 will now be described in greater detail. Hand piece 20 has a proximal end 21 and a distal end 22, a fluid supply connection 23 and a vacuum supply connection 24 preferably located at the proximal end, and a fluid supply fitting and a vacuum supply fitting at the distal end (to interface with the cannula). The hand piece 20 routes the heated fluid from the fluid supply to the supply tubes 35 in the cannula and routes the vacuum from the vacuum source 14 to the cavity in the cannula, to evacuate material from the cavity.

In some embodiments, a cooling fluid supply 6 may be used to dampen the heat effect of the heated fluid stream in the surgical field. In these embodiments, the handpiece also routes the cooling fluid into the cannula 35 using appropriate fittings at each end of the handpiece. In these embodiments, a cooling fluid metering device 13 may optionally be included. The hand piece 20 may optionally include operational and ergonomic features such as a molded grip, vacuum supply on/off control, heat source on/off control, alternate cooling fluid on/off control, metering device on/off control, and fluid pressure control. Hand piece 20 may also optionally include operational indicators including cannula suction orifice location indicators, temperature and pressure indicators, as well as indicators for delivered fluid volume, aspirated fluid volume, and volume of tissue removed. Alternatively, one or more of the aforementioned controls may be placed on a separate control panel.

The distal end 22 of hand piece 20 is configured to mate with the cannula 30. Cannula 30 comprises a hollow tube of surgical grade material, such as stainless steel, that extends from a proximal end 31 and terminates in a rounded tip at a distal end 32. The proximal end 31 of the cannula 30 attaches to the distal end 22 of hand piece 20. Attachment may be by means of threaded screw fittings, snap fittings, quick-release fittings, frictional fittings, or any other attachment connection known in the art. It will be appreciated that the attachment connection should prevent dislocation of cannula 30 from hand piece 20 during use, and in particular should prevent unnecessary movement between cannula 30 and hand piece 20 as the surgeon moves the cannula hand piece assembly in a back and forth motion approximately parallel to the cannula longitudinal axis 33.

The cannula may include designs of various diameters, lengths, curvatures, and angulations to allow the surgeon anatomic accuracy based upon the part of the body being treated, the amount of fat extracted as well as the overall patient shape and morphology. This would include cannula diameters ranging from the sub millimeter range (0.25 mm) for delicate precise liposuction of small fatty deposits to cannulas with diameters up to 2 cm for large volume fat removal (i.e. abdomen, buttocks, hips, back, thighs etc.), and lengths from 2 cm for small areas (i.e. eyelids, cheeks, jowls, face etc.) up to 50 cm in length for larger areas and areas on the extremities (i.e. legs, arms, calves, back, abdomen, buttocks, thighs etc.). A myriad of designs include, without limitation, a C-shaped curves of the distal tip alone, S-shaped curves, step-off curves from the proximal or distal end as well as other linear and nonlinear designs. The cannula may be a solid cylindrical tube, articulated, or flexible.

Each of the suction orifice ports 37 includes a proximal end 38, a distal end 39, and a suction orifice port perimeter 40. Although the illustrated suction orifices are oval or round, in alternative embodiments they may be made in other shapes (e.g., egg shaped, diamond or polygonal shaped, or an amorphous shape). As depicted in FIG. 3, the suction orifice ports 37 may be arranged in a linear fashion on one or more sides of cannula 30. Alternatively, the suction orifice ports 37 may be provided in a multiple linear arrangement, as depicted in FIG. 4. Optionally, the dimensions or shape of each suction orifice port may change, for example, from the most distal suction orifice port to the most proximal, as illustrated in FIG. 4, where the diameter of each suction orifice port may decrease in succession from the distal port to the proximal port.

In some embodiments, the suction orifice perimeter edge 40 is configured to present a smooth, unsharpened edge to discourage shearing, tearing or cutting of the target fatty tissue. Because the target tissue is liquefied/gellified/softened; the cannula 30 does not need to shear tissue as much as found in traditional liposuction cannulas. In these embodiments, the perimeter edge 40 is duller and thicker than typically found in prior-art liposuction cannulas. In alternative embodiments, the cannula may use shearing suction orifices, or a combination of reduced-shearing and shearing suction orifice ports. The suction orifice port perimeter edge 40 of any individualized suction orifice port may also be configured to include a shearing surface or a combination of shearing and reduced-shearing surfaces, as appropriate for the particular application.

Figure 1:
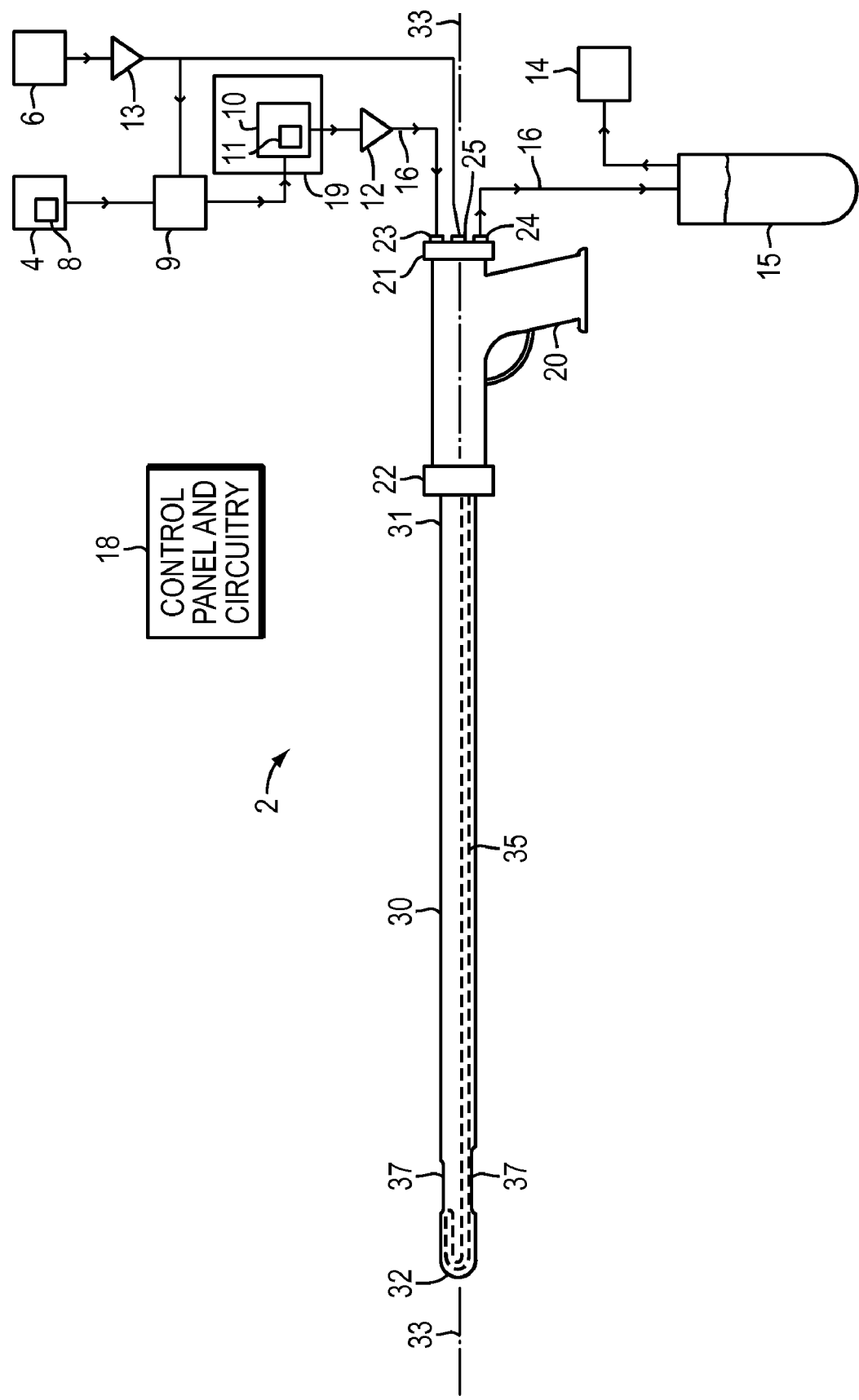
FIG. 1 shows an embodiment of a tissue liquefaction system.
Figure 6:
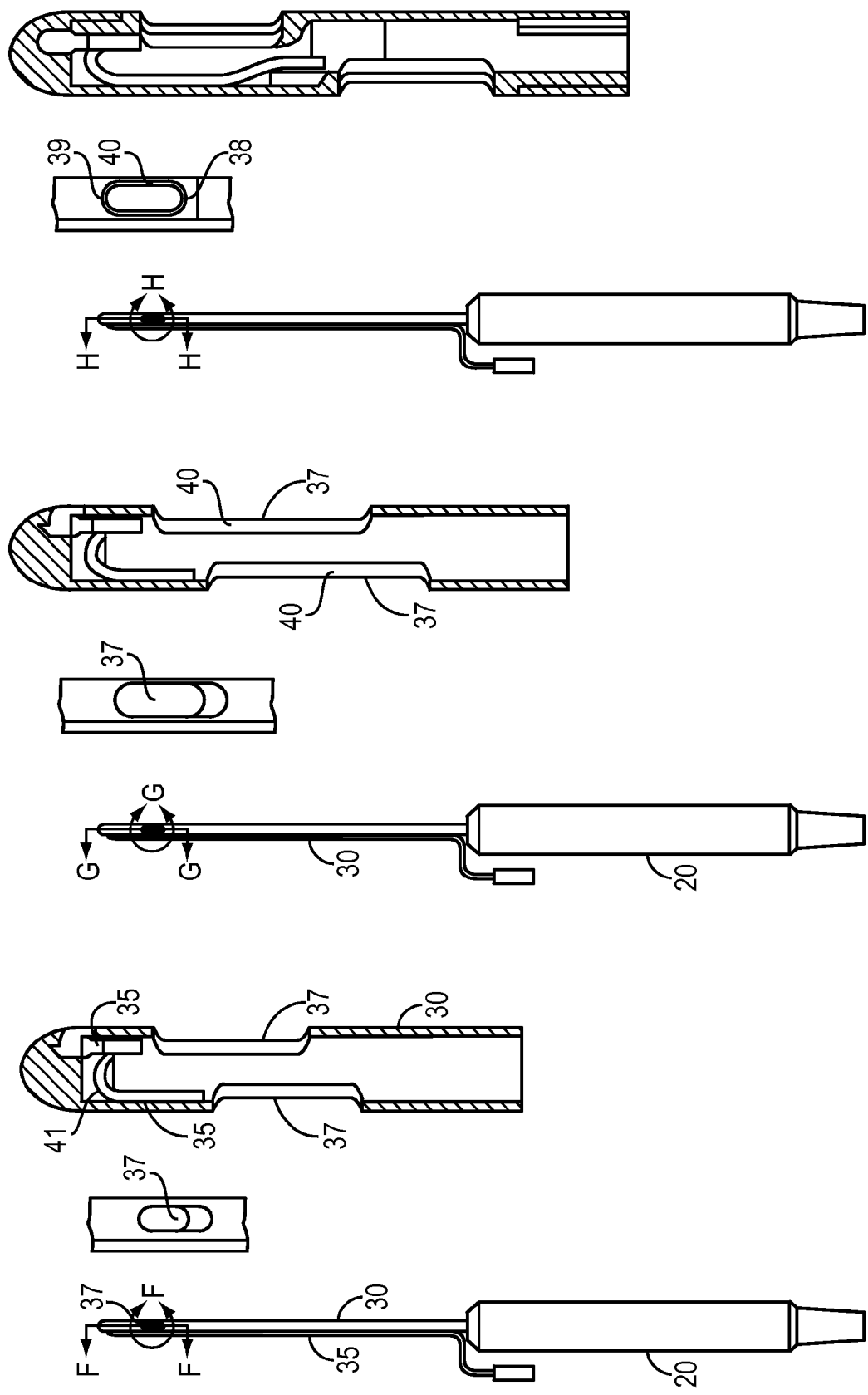
FIG. 6 shows some variations of the distal end of the cannula.

Using between one and six suction orifices 37 is preferable for subcutaneous fat, and using two or three suction orifices is more preferable. The suction orifices may be made in different shapes, such as round or oblong. FIG. 6 shows some exemplary suction orifices of different size. Cross section F is shown with a standard shearing orifice port 37. Cross section G has a larger shearing orifice port 37, while cross section H has a perimeter with a smooth and unsharpened edge to discourage shearing. When oblong suction orifices are used, the long axis should preferably be oriented substantially parallel to the distal-to-proximal axis. The suction orifices should not be too large, because with smaller suction orifices less fat is suctioned into the cannula for a given bolus of energy. On the other hand they should not be too small, to permit the fatty tissue to enter. A suitable size range for circular suction orifices is between about 0.04" and 0.2". A suitable side for oblong suction orifices is between about 0.2"×0.05" and about ½"×?". The size of the suction orifices can further be varied for different applications depending on the surgeon's requirements. More extensive areas to be suctioned may require larger orifices which require more shearing surface.

As shown in FIGS. 7-13, the surface area of a unit length of the suction path can be calculated by multiplying the total perimeter of the suction path by a unit length. An exemplary perimeter of the suction path is p(4.115 mm), which when multiplied by 1 mm length, gives a unit length area of 12.9 mm$^2$. FIG. 7 shows the diameter of the inside of the suction path (which would then be multiplied by p to give the perimeter length and then by a unit length of 1 mm to give the surface area of 12.93). For the embodiment shown in FIG. 7, the resistance ratio of the suction path calculates to be 12.92 mm$^2$/13.30 mm$^2$=0.97. And the resistance ratio of the fluid path (both tubes included) calculates to be: 5.10 mm$^2$/1.04 mm$^2$=4.90. Comparing resistive ratios, with the first passage being defined as the suction path, in the FIG. 7 embodiment, we see that the comparative resistance ratio is 0.97/4.90=0.20.

Figure 10:
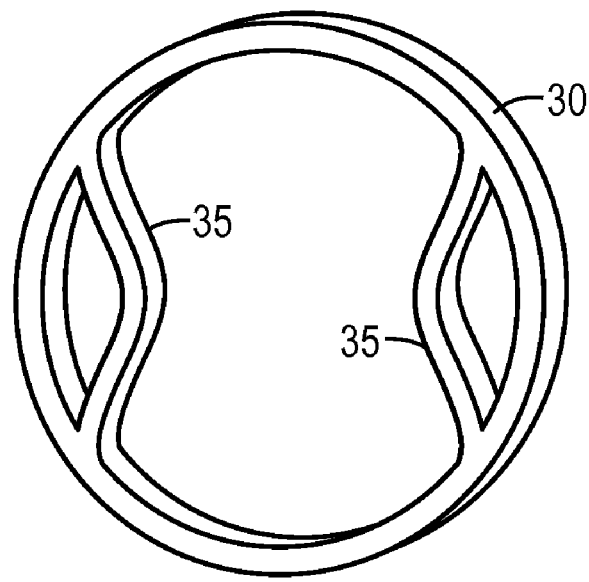
FIG. 10 shows a cannula configuration with two internal fluid supply tubes.
Figure 11:
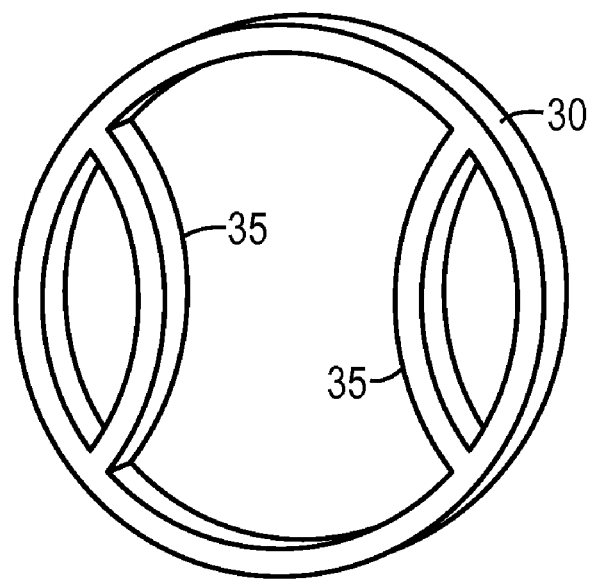
FIG. 11 shows a cannula having two fluid supply paths internal to the suction path.
Figure 12:
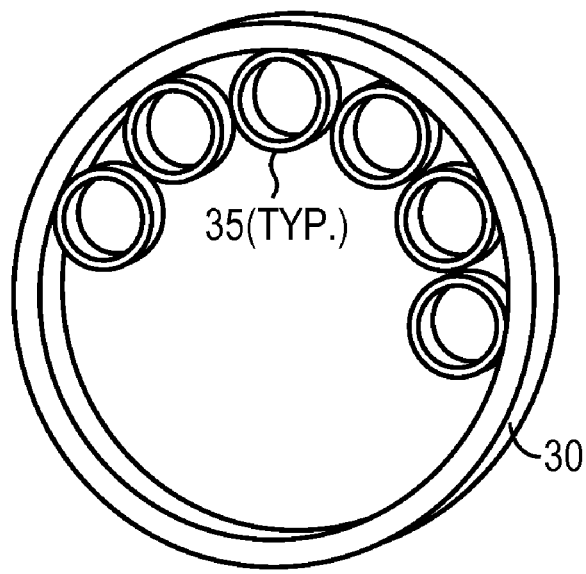
FIG. 12 shows a cannula with six fluid supply paths internal to the suction path.
Figure 13:
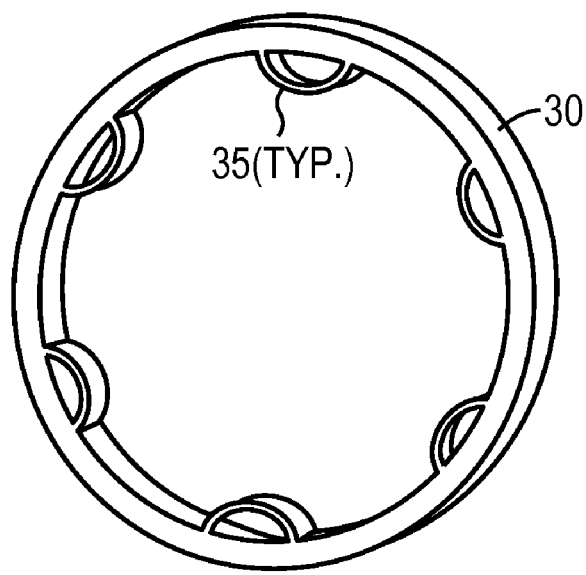
FIG. 13 shows an alternative cannula configuration with six internal fluid supply paths.

For the embodiment shown in FIG. 8, the calculated resistance ratio of the suction path is 1.68 and the calculated resistance ratio of the fluid path (both tubes included) is 4.92. Accordingly, the comparative resistance ratio is 0.38. Similarly, in FIG. 9, the suction resistance ratio is 1.11 and the fluid resistance ratio 4.61, so the comparative resistance ratio is 0.24. In FIG. 10, the suction resistance ratio is 1.20 and the fluid resistance ratio 5.98, so the comparative resistance ratio equals 0.20. In FIG. 11, the suction resistance ratio is 1.31 and the fluid resistance ratio is 4.65, so the comparative resistance ratio is 0.28. In FIG. 12, the suction resistance ratio is 2.25 and the fluid resistance ratio 7.88, so the comparative resistance ratio is 0.29. In FIG. 13, the suction resistance ratio is 1.23 and the fluid resistance ratio is 10.23, so the comparative resistance ratio is 0.12.

The general principles described above may be optimized for removing visceral fat from a subject's body. However, since visceral fat is located on and around organs that are more delicate than the tissue in which subcutaneous fat is found, care must be taken to minimize trauma to the relevant anatomical regions, to permit removal the visceral fat without causing damage or trauma to the adjacent internal organs. For example, the orifice ports should preferably have blunt edges (as opposed to sharp edges) for this use, so as to avoid shearing and cutting of tissue, and the pressure and temperature ranges should be selected to avoid trauma.

The straight cannula embodiments described above may be used for removing visceral fat. Preferably, the cannula tubing is constructed from cylindrical, elliptical, or flat face tubing, with no exaggerated blunt faces. Suitable materials for the cannula body include surgical grade metallic materials like 304 and 316 stainless steel, as well as shape memory and super elastic metallic materials like Nitinol. The cannula can also be made of non-metallic materials like Peek, polycarbonate, high density polyethylene, nylon, and other high durometer plastics.

The cannula can be constructed with and without an outer sleeve that is braided, coiled, or continuous. The sleeve can be made out of Teflon or other flexible polymeric materials like urethane, nylon, and others. The sleeve can also be made of thin wall metallic materials like stainless steel and Nitinol in a non-continuous (coil or braid) to provide flexibility. The cannula can also be constructed of a multi layer polymer and metallic combination, such as a Teflon base inner layer with a metallic braid or coil middle layer and a polymeric outer layer like nylon or urethane. This would be similar to existing coronary guiding catheter technologies like the one used in Cordis Vista Brite Tip Guiding Catheters and endoscopes like the one used in the Olympus Fiber Optic Lines (BF-XP60).

Suitable dimensions for the cannula diameter range from 2.0 mm for small delicate fatty deposits to 20 mm for large volume fat removals like Omentectomy. For open surgical procedures the entire range of cannula sized can be used. For laparoscopic or approaches requiring passage through other conduits or trocar sheaths, the cannula diameter range should be 2.0-12.0 mm sizes, based on currently used abdominal trocar and access cannula sizes.

Suitable dimensions for the cannula diameter length range from 2.0 cm for open surgical procedures to 50 cm for laparoscopic or procedures requiring access through other cannula sheaths.

The cannula preferably has between 1 and 6 orifice ports, which may be spaced on the same side or around the circumference. More preferably, between 1 and 4 orifice ports are used, all positioned on the bottom (i.e., the tissue contact surface). The most preferred visceral cannula has 1 or 2 openings, all positioned on the bottom so as to minimize pulling in non-target tissues and allow greater control to the surgeon.

The opening shapes can be circular, elliptical, rectangular, and triangular or many other geometrical shapes. One preferred opening shape is an elongated elliptical shape. The size of the opening can vary for any given cannula diameter and length. The opening diameter is preferably smaller than half of the cannula diameter and the length may be order of three quarters of the cannula diameter or less. Preferably, the orifice ports have blunt edges to minimize any trauma to non-target tissues.

Optionally, one or more bends may be incorporated into the cannula, as shown in FIGS. 16A and 16B. Preferably the distal-most bend is proximal to the proximal-most orifice port. The bends are preferably configured to aid the surgeon in the insertion and manipulation of the cannula, to conform to the particular anatomic region being treated. The bends may either be abrupt (e.g., bent like a hockey stick), as illustrated in FIGS. 16A and 16B, or have a larger radius of curvature (e.g., bent like the handle of a walking cane), depending on the anatomic region being treated.

FIGS. 16A and 16B illustrate two embodiments of a cannula for visceral fat applications, and similar reference numbers are used to describe both of those embodiments. Cannula 30 comprises a hollow tube that extends from a proximal end 31 and terminates in a rounded tip at a distal end 32. FIG. 16A shows a cannula with a single bend 46, whereas FIG. 16B shows a cannula with two bends 46, and additional bends may be included in alternative embodiments if so desired. The bends 46 are preferably proximal to all the orifice ports 37. In the bent embodiments, the bend angle is preferably between 5 and 85 degrees. The optimum bend angle will depend on the particular procedure being performed. For open surgical procedures, larger angles (e.g., between 45 and 85 degrees) are more suitable, more preferably between 55 and 75 degrees. For laparoscopic procedures that require the cannula to be inserted through other cannulas or sheaths, smaller angles (e.g., between 5 and 45 degrees) are more suitable, more preferably between 15 and 35 degrees. For open surgical procedures, the length of the distal section of the cannula past the bend is preferably between 1 and 4 inches. For laparoscopic procedures, the length of the distal section of the cannula past the bend is preferably between 1 and 2 inches.

In the illustrated embodiments, the cannula 30 has two orifice ports 37 located near the distal region of the cannula 30 and proximal to the distal tip 32, disposed on opposite sides of the cannula 30. However in alternative embodiments, the orifice ports 37 may be positioned in different configurations about the perimeter of the distal region of cannula 30. For example, a different number of orifice ports (e.g., 1-6) may be used, disposed at different angles (e.g., 70° apart) or all on the same side (i.e., 0° apart).

The orifice ports 37 are configured to allow fatty tissue to enter the port in response to low pressure within the cannula shaft created by vacuum supply 14. Orifice ports 37 include a proximal end 38, a distal end 39, and an orifice port perimeter edge 40. Orifice ports 37 may take a generally circular, oval or egg shape, diamond or polygonal shape, or an amorphous shape. In the illustrated embodiments, the orifice ports 37 are oval and are all the same size. In alternative embodiments, the dimensions or shape of the orifice ports may vary within a single cannula, like the cannula shown in FIG. 4, in which the diameter of each orifice port decreases in succession from the distal end to the proximal end.

In both the straight and bent embodiments, the cannula may be made of round tubing or tubing with one or more flat surfaces. The distal end of the cannula may be integrally formed as a continuation of the shaft or it can be a two piece construction, with a metal or polymer tip affixed to the end of the shaft. Polymer tips can be advantageous because they are softer than metal. Examples of suitable materials for the tip include, but are not limited to nylon and high density polyethylene.

In alternative embodiments (not shown), one or more articulation joints may be incorporated into the cannula. Preferably, these articulation joints are provided proximal to the proximal-most orifice. One suitable way to implement these articulating embodiments is to replace a portion of the cannula from a point that is proximal of the proximal-most orifice with a flexible tubing, and then running that flexible tubing through a conventional articulation joint. In these embodiments, the flexible tubing should be selected or reinforced so as not to collapse under the vacuums expected to be encountered. Examples of suitable articulation joints can be found in U.S. Pat. Nos. 4,108,211 and 7,090,637, each of which is incorporated herein by reference as if set forth herein in its entirety. Other examples include the bending mechanisms used in endoscopes like the Olympus Fiber Optic Lines (BF-XP60) and in other articulating devices like the Medtronic Heart Wall Ablation Catheters (RF Conductr (MC) Series). Any suitable conventional control mechanism may be used to bend the articulation joints, depending on the articulation joint that is used. Examples include foot pedals and hand controls.

When articulation joints with bending mechanisms are incorporated, the operator is able to control the position of distal end of the cannula. For example, if an articulation joint with a single degree of freedom is used, the operator would be able to bend the joint back and forth, like a windshield wiper so as to move the distal end in an arc. A suitable range of motion is 90° of bending (i.e., ±45°), but smaller or larger articulation angles may be implemented, e.g., up to 180° of bending (i.e., ±90°).

If an articulation joint with two perpendicular degrees of freedom is used, the operator would be able to bend the joint back and forth, and would also be able to move the distal end of the probe up and down in a direction that is perpendicular to the plane of the wiping motion. These embodiments permit manipulation of the cannula's distal end in three-dimensional space, providing additional fine-tuned control of movement, which can be particularly desirable when removing visceral fat from around intestinal structures. A suitable range of motion in the up/down direction is 45° of bending, but smaller or larger articulation angles may be implemented, e.g., 80° of bending. Optionally, the bending may be controlled by a mechanized, motorized unit under direct control of the surgeon.

The visceral fatty tissue lipectomy of the present invention should be target tissue-specific so as to remove the visceral fat without damaging the surrounding organs and tissue. To accomplish this, the temperature of the solution is preferably between 75 and 250° F., more preferably between 75 and 190° F., still more preferably between 100 and 140° F., and most preferably about 120° F. The stream pressure is preferably between 300 and 2000 psi, more preferably between 600 and 1300 psi, still more preferably between 900 and 1300 psi, and most preferably about 1100 psi. The fluid should preferably be delivered in pulses, with a preferred pulse rate between 25 and 60 pulses per second, more preferably about 40 pulses per second. The preferred duty cycle for these pulses is between about 30 and 80%, more preferably about 30% to minimize the amount of waste fluid that is generated. The preferred rise rate for the pulses is about 1 millisecond or less. The aspiration (vacuum) is preferably between ⅓ and 1 atmosphere, and more preferably between ⅓ and ¾ atmosphere.

In the most preferred embodiments for removing visceral fat, the temperature of the solution is between 100 and 140° F., and it is delivered in pulses at a stream pressure between 900 and 1300 psi at a pulse rate between 25 and 60 pulses per second. This combination of parameters provides good tissue differentiation, so as to facilitate removal of the visceral fat without causing trauma to the delicate anatomic structures in the vicinity.

To perform removal of visceral fat, the cannula is inserted into the abdomen via an open surgical procedure or through a smaller laparoscopic incision. In the latter case, the visceral fat is preferably visualized by a laparoscopic camera using any suitable conventional visualization technology.

Optionally, surgical field cleaning fluids such as water or saline may be delivered to the site being treated. Alternatively or in addition, a small amount of liposuction tumescent fluid (containing, e.g., epinephrine, lidocaine, levorphonal, phenylephrine, athyl-andrianol, ephedrine, or other vasoconstrictors and/or xylocalne, marcaine, nesacaine, Novocain, diprivan, ketalar, ladocaine, or other anesthetic agents and/or other suitable chemicals) may be introduced into the region that is being treated. One suitable way to introduce such fluids into the desired region is to include a dedicated conduit that is built into the cannula, with a forward-facing exit port similar to the port 45 shown in FIGS. 5 and 5A. In alternative embodiments a separate catheter may be used to introduce the desired fluids. These infusions are preferably implemented using low pressure peristaltic type pumping system, at a pressure less than 200 psi, and at an infusion flow rate between 50 and 600 ml min.

The visceral fat is preferably removed using a slow, controlled, precise movement of the cannula over the visceral fat. Only minor bleeding is expected, and that can be controlled by well established techniques known in the surgical art of laparoscopic or open surgery.

The embodiments that are optimized for removing visceral fat may be used during gastric bypass surgeries, or as stand alone procedures for obese patients who do not qualify for gastric bypass surgery, especially for individuals with poorly controlled diabetes mellitus type II. Additionally, visceral fatty tissue lipectomy described in connection with these embodiments can be performed as a medical procedure for the prevention of diabetes mellitus type II and cardiovascular disease in patients with significant stores of visceral fat.

The embodiments described above may be used in various liposuction procedures including, without limitation, liposuction of the face, neck, jowls, eyelids, posterior neck (buffalo hump), back, shoulders, arms, triceps, biceps, forearms, hands, chest, breasts, abdomen, abdominal etching and sculpting, flanks, love handles, lower back, buttocks, banana roll, hips, saddle bags, anterior and posterior thighs, inner thighs, mons pubis, vulva, knees, calves, shin, pretibial area, ankles and feet. They may also be used in revisional liposuction surgery to precisely remove residual fatty tissues and firm scar tissue (areas of fibrosis) after previous liposuction.

The embodiments described above may also be used in conjunction with other plastic surgery procedures in which skin, fat, fascia and/or muscle flaps are elevated and/or removed as part of the surgical procedure. This would include, but is not limited to facelift surgery (rhytidectomy) with neck sculpting and submental fat removal, jowl excision, and cheek fat manipulation, eyelid surgery (blepharoplasty), brow surgery, breast reduction, breast lift, breast augmentation, breast reconstruction, abdominoplasty, body contouring, body lifts, thigh lifts, buttock lifts, arm lifts (brachioplasty), as well as general reconstructive surgery of the head, neck, breast abdomen and extremities. It will be further appreciated that the embodiments described above have numerous applications outside the field of liposuction.

The embodiments described above may be used in skin resurfacing of areas of the body with evidence of skin aging including but not limited to sun damage (actinic changes), wrinkle lines, smokers' lines, laugh lines, hyper pigmentation, melasma, acne scars, previous surgical scars, keratoses, as well as other skin proliferative disorders.

The embodiments described above may target additional tissue types including, without limitation, damaged skin with thickened outer layers of the skin (keratin) and thinning of the dermal components (collagen, elastin, hyaluronic acid) creating abnormal, aged skin. The cannula would extract, remove, and target the damaged outer layers, leaving behind the healthy deep layers (a process similar to traditional dermabrasion, chemical peels (trichloroacetic acid, phenol, croton oil, salicyclic acid, etc.) and ablative laser resurfacing (carbon dioxide, erbium, etc.) The heated stream would allow for deep tissue stimulation, lightening as well as collagen deposition creating tighter skin, with improvement of overall skin texture and/or skin tone with improvements in color variations. This process would offer increased precision with decreased collateral damage over traditional methods utilizing settings and delivery fluids which are selective to only the damaged target tissue.

Other implementations include various distal tip designs and lighter pressure settings that may be used for tissue cleansing particularly in the face but also applied to the neck, chest and body for deep cleaning, exfoliation and overall skin hydration and miniaturization. Higher pressure settings may also be used for areas of hyperkeratosis, callus formation in the feet, hands knees, and elbows to soften, hydrate and moisturize excessively dry areas.

Additional tissue removal procedures may be accomplished by various other embodiments. For example, cannula designs with lower pressure settings including lower suction pressure and an atraumatic stream with gentle boluses may be used to selectively remove viable fat cells (adipocytes) which can be extracted and processed for re-injection into areas of fat deficiency. This would include, without limitation, areas around the face, brow, eyelids, tear troughs, smile lines, nasolabial folds, labiomental folds, cheeks, jaw line, chin, breast, chest abdomen, buttocks, arms, biceps, triceps, forearms, hands, flanks, hips, thighs, knees, calves, shin, feet, and back. A similar method may be used to address post liposuction depressions and/or concavities from over aggressive liposuction. Other procedures utilizing a similar method include; without limitation, breast augmentation, breast lifts, breast reconstruction, general plastic surgery reconstruction, facial reconstruction, reconstruction of the trunk and/or extremities.

Additional uses include tissue removal in the spine or spinal nucleotomy. The cannula used in spinal nucleotomy procedures includes heated solution supply tubes within the cannula as described above. The cannula further includes a flexible tip capable of moving in multiple axes, for example, up, down, right and left. Because of the flexible tip, a surgeon may insert a cannula through an opening in the annulus fibrosis and into the central area, where the nucleus pulpous tissue is located. The surgeon can then direct the cannula tip in any direction. Using the cannula in this manner the surgeon is able to clean out the nucleus pulpous tissue while leaving the annulus fibrosis and nerve tissue intact and unharmed.

In another implementation, the present design can be incorporated in to an endovascular catheter for removal of vascular thrombus and atheromatous plaque, including vulnerable plaque in the coronary arteries and other vasculature.

In another implementation, a cannula using the present design can be used in urologic applications that include, but are not limited to, trans-urethral prostatectomy and trans-urethral resection of bladder tumors.

In another implementation, the present design can be incorporated into a device or cannula used in endoscopic surgery. An example of one such application is chondral or cartilage resurfacing in arthroscopic surgery. The cannula can be used to remove irregular, damaged, or torn cartilage, scar tissue and other debris or deposits to generate a smoother articular surface. Another example is in gynecologic surgery and the endoscopic removal of endometrial tissue in proximity to the ovary, fallopian tubes or in the peritoneal or retroperitoneal cavities.

In yet a further implementation to treat chronic bronchitis and emphysema (COPD), the cannula can be modified to be used in the manner a bronchoscope is used; the inflamed lining of the bronchial tubes would be liquefied and aspirated, thereby allowing new, healthy bronchial tube tissue to take its place.

The various embodiments described each provide at least one of the following advantages: (1) differentiation between target tissue and non-target tissue; (2) clog resistance, since the liquid projected in a distal-to-proximal direction across the suction orifices, which generally prevents the suction orifice or the cannula from clogging or becoming obstructed; (3) a reduction in the level of suction compared to traditional liposuction, which mitigates damage to non-target tissue; (4) a significant reduction in the time of the procedure and the amount of cannula manipulation required; (5) a significant reduction in surgeon fatigue; (6) a reduction in blood loss to the patient; and (7) improved patient recovery time because there is less need for shearing of fatty tissue during the procedure.

Although the present invention has been described in detail with reference to certain implementations, other implementations are possible and contemplated herein.

All the features disclosed in this specification may be replaced by alternative features serving the same, equivalent, or similar purpose, unless expressly stated otherwise. Thus, unless expressly stated otherwise, each feature disclosed is one example only of a generic series of equivalent or similar features.

What is claimed is:

1. A method of removing visceral fat from a subject using a cannula that has a longitudinal axis that runs in a proximalto-distal direction, the cannula having an interior cavity and an orifice that is configured to permit material to enter the interior cavity, the method comprising the steps of:
- generating a negative pressure in the interior cavity so that the negative pressure draws a portion of the visceral fat, in a direction that is perpendicular to the longitudinal axis, into the interior cavity via the orifice, wherein the orifice is substantially parallel to the longitudinal axis;
- delivering fluid, via a conduit, so that the fluid exits the conduit within the interior cavity and impinges against the portion of the visceral fat that was drawn into the interior cavity, wherein the fluid is delivered as a series of pulses at a pressure between 600 and 1300 psi and at a temperature between 100° F. and 140° F., so as to soften, liquefy, or gellify the visceral fat; and
- suctioning away the visceral fat that has been softened, liquefied, or gellified.

2. The method of claim 1, wherein the fluid is delivered at a temperature of about 120° F.

3. The method of claim 1, wherein the fluid is delivered at a pulse rate of between 25 and 60 pulses per second.

4. The method of claim 3, wherein the pulses are delivered with a duty cycle between 30 and 80 percent.

5. The method of claim 4, wherein the fluid is delivered at a temperature of about 120° F. and the fluid is delivered as a series of pulses at a pressure between 900 and 1300 psi.

6. The method of claim 1, wherein the fluid is traveling in a substantially distal to proximal direction just before it impinges against the portion of the visceral fat that was drawn into the interior cavity.

7. The method of claim 1, wherein the fluid is delivered as a series of pulses at a pressure between 900 and 1300 psi.

* * * * *

UNITED STATES PATENT AND TRADEMARK OFFICE
CERTIFICATE OF CORRECTION

| | | |
|---|---|---|
| PATENT NO. | : 8,366,700 B2 | Page 1 of 1 |
| APPLICATION NO. | : 12/366983 | |
| DATED | : February 5, 2013 | |
| INVENTOR(S) | : Andrew et al. | |

It is certified that error appears in the above-identified patent and that said Letters Patent is hereby corrected as shown below:

In the Claims

Column 15
line 14, (claim 1) change "F." to --F-- (both occurrences)

Column 16
line 8, (claim 5) change "F." to --F--

Signed and Sealed this
Twelfth Day of November, 2013

Teresa Stanek Rea
*Deputy Director of the United States Patent and Trademark Office*